(12) United States Patent
Foreman

(10) Patent No.: US 6,399,114 B2
(45) Date of Patent: Jun. 4, 2002

(54) NUTRITIONAL SYSTEM FOR NERVOUS SYSTEM DISORDERS

(75) Inventor: David J. Foreman, Chesterfield, VA (US)

(73) Assignee: C & D Foreman, Inc., Chesterfield, VA (US)

( * ) Notice: Subject to any disclaimer, the term of this patent is extended or adjusted under 35 U.S.C. 154(b) by 0 days.

(21) Appl. No.: 09/865,040

(22) Filed: May 24, 2001

Related U.S. Application Data

(60) Provisional application No. 60/207,665, filed on May 26, 2000.

(51) Int. Cl.[7] .............................................. A61K 35/78
(52) U.S. Cl. ..................... 424/725; 424/93.3; 424/93.4; 424/94.1; 424/94.2; 424/195.17; 424/630; 424/655; 424/682; 424/732; 424/744; 424/752; 424/757; 424/764; 424/765; 424/770; 514/52; 514/77
(58) Field of Search ................................. 424/725, 93.3, 424/93.4, 195.17, 630; 514/52, 77

(56) References Cited

U.S. PATENT DOCUMENTS

| | | | | |
|---|---|---|---|---|
| 4,500,515 A | * | 2/1985 | Libby | |
| 4,806,368 A | * | 2/1989 | Reddy | |
| 5,437,880 A | * | 8/1995 | Takaichi et al. | |
| 5,567,424 A | * | 10/1996 | Hastings | |
| 5,569,458 A | * | 10/1996 | Greenberg | |
| 5,730,988 A | * | 3/1998 | Womack | |
| 5,877,171 A | * | 3/1999 | McLeod | |
| 5,902,797 A | * | 5/1999 | Bell et al. | |
| 5,905,075 A | * | 5/1999 | Harpe et al. | |

* cited by examiner

Primary Examiner—Leon B. Lankford, Jr.
Assistant Examiner—Ruth A. Davis
(74) Attorney, Agent, or Firm—Williams Mullen Clark & Dobbins

(57) ABSTRACT

A novel composition for treating nervous system disorders. The composition is formed by preparing a mixture comprising an effective amount of vitamin B-6, folic acid, vitamin C, magnesium, vitamin B-3, copper, probiotics, fructo-oligosaccharide (FOS), betaine, pancreatin, papain, pepsin, vitamin B-1, vitamin B-2, vitamin B-12, biotin, pantothenic acid, chromium polynicotinate and a digestive support ingredient selected from the group consisting of dandelion root, juniper, aloe vera, burdock, ginger root, artichoke, and kelp. Other ingredients may include: beta carotene, vitamin E, selenium, zinc, sea vegetation, alfalfa, trace minerals and molybdenum.

13 Claims, No Drawings

NUTRITIONAL SYSTEM FOR NERVOUS SYSTEM DISORDERS

CROSS REFERENCE TO RELATED APPLICATION

The present application claims priority from U.S. Provisional Application Ser. No. 60/207,665, filed May 26, 2000.

BACKGROUND OF THE INVENTION

1. Technical Field of the Invention

The present invention pertains to the field of nutritional formulas. Specifically, the present invention pertains to an improved formula for nervous system disorders.

2. Discussion of the Related Art

There are many disorders that affect the proper functioning of the nervous system. Examples of these disorders include autism, ADD, ADHD, hyperactivity disorder, and depression. People who suffer from these disorders often have common secondary symptoms including allergies, sluggish digestion, weak immune function and poor diet.

Treatment for these various nervous system disorders include the use of synthetic drugs. Specifically, for ADD and ADHD mild central nervous system stimulant drugs such as Ritalin®, Cylert® and Dexedrine® have been used. These drugs are not always successful. Moreover, such drugs may lead to undesirable side effects such as loss of appetite, insomnia, headaches, stomachaches, drowsiness and cardiac arrhythmia.

There is, therefore, a need for new treatments of nervous system disorders that avoid the disadvantages of the known treatments. It is an objective of the present invention to provide such treatments. More specifically, it is an objective of the present invention to provide a new treatment for nervous system disorders, better than known methods, while at the same time avoiding the side effects observed with traditional drugs. Additional objects and advantages of the present invention are apparent from the specification which follow.

SUMMARY OF THE INVENTION

According to the present invention, the foregoing and additional objects are obtained by providing a novel composition for treating nervous system disorders. The composition is formed by preparing a mixture comprising an effective amount of vitamin B-6, folic acid, vitamin C, magnesium, vitamin B-3, copper, probiotics, fructo-oligosaccharide (FOS), betaine, pancreatin, papain, pepsin, vitamin B-1, vitamin B-2, vitamin B-12, biotin, pantothenic acid, chromium polynicotinate and a digestive support ingredient selected from the group consisting of dandelion root, juniper, aloe vera, burdock, ginger root, artichoke, and kelp. Other ingredients may include: beta carotene, vitamin E, selenium, zinc, sea vegetation, alfalfa, trace minerals and molybdenum.

In a preferred embodiment, the composition is formed by preparing a mixture comprising an effective amount of beta carotene, vitamin E, selenium, vitamin B-6, folic acid, vitamin C, magnesium, vitamin B-1, vitamin B-2, niacinamide, vitamin B-12, zinc, copper, biotin, pantothenic acid, dandelion root, acidophilus dairy free, bifidus dairy free, FOS powder, chromium polynicotinate, betaine HCl, pancreatin, papain, and pepsin.

The effective range amount of each ingredient for sixty pounds of body weight is as follows: 1,250–25,000 IU beta carotene, 25–400 IU vitamin E, 25–100 mcg selenium, 100–500 mg vitamin B-6, 400–800 mcg folic acid, 250–1,000 mg vitamin C, 125–500 mg magnesium, 12.5–50 mg vitamin B-1, 12.5–50 mg vitamin B-2, 15–60 mg niacinamide, 12.5–50 mcg vitamin B-12, 8–50 mg zinc, 250–1,000 mcg copper, 25–100 mcg biotin, 12.5–50 mg pantothenic acid, 250–2,000 mg dandelion root, 500–3,000 million cfu acidophilus dairy free, 500–3,000 million cfu bifidus dairy free, 250–500 mg FOS powder, 100–200 mcg chromium polynicotinate, 15–100 mg betaine HCl, 125–1,000 mg pancreatin, 50–250 mg papain, and (1:3000) 15–100 mg pepsin.

In a preferred embodiment, the effective amount of each ingredient for sixty pounds of body weight is as follows: 5000 IU beta carotene, 50 IU vitamin E, 25 mcg selenium, 500 mg vitamin B-6, 400 mcg folic acid, 500 mg vitamin C, 250 mg magnesium, 25 mg vitamin B-1, 25 mg vitamin B-2, 30 mg niacinamide, 25 mcg vitamin B-12, 10 mg zinc, 500 mcg copper, 50 mcg biotin, 25 mg pantothenic acid, 250 mg dandelion root, 500 million cfu acidophilus dairy free, 500 million cfu bifidus dairy free, 250 mg FOS powder, 100 mcg chromium polynicotinate, 30 mg betaine HCl, 250 mg pancreatin, 100 mg papain, and (1:3000) 30 mg pepsin.

DETAILED DESCRIPTION OF THE PREFERRED EMBODIMENT

The composition of the present invention acts to assist in treatment of nervous system disorders. The concept of the composition is to give the body the tools it needs to digest, absorb, manufacture and utilize nutrients that help in the formation of neurotransmitters. This composition has a balancing effect in the body.

The components may be mixed in any order to prepare the composition. The composition may comprise the same components that were added to the mixture, or items from which the components may be derived.

The components of the composition are in a form that are systemically absorbable by a human. The composition may be in tablet, capsule or powder form. The powder can be mixed in water or other consumable liquid and may be flavored for taste.

Each capsule contains a unit dose of each component. An effective dose is one capsule per approximate 10 pounds of body weight. Said dose is preferably taken divided among meals and snacks eaten during the day. For example, a 60 pound child would take 6 capsules daily—2 with breakfast, 2 with lunch, 2 with dinner. A dose in powder form is one teaspoon per 20 pounds of body weight.

The components may be formulated for administration into one composition containing all the components. Alternatively, the components may be formulated into more than one composition, each which contains one or more of the components. In addition, each component may constitute a separate composition, and be administered separately. It is preferable to administer the smallest number of separate compositions. Yeast, wheat, corn and gluten products are avoided as fillers.

In the discussions below, all numbers are approximate, unless otherwise stated. MG stands for milligram, MCG stands for microgram and IU represents international units and CFU means colony forming units.

According to the present invention, the foregoing and additional objects are obtained by providing a novel composition for treating nervous system disorders. The composition is formed by preparing a mixture comprising an effective amount of vitamin B-6, folic acid, vitamin C, magnesium, vitamin B-3, copper, probiotics, fructo-oligosaccharide (FOS), betaine, pancreatin, papain, pepsin, vitamin B-1, vitamin B-2, vitamin B-12, biotin, pantothenic acid, chromium polynicotinate and a digestive support ingredient selected from the group consisting of dandelion root, juniper, aloe vera, burdock, ginger root, artichoke and kelp. Other ingredients may include: beta carotene, vitamin E, selenium, zinc, sea vegetation, alfalfa, trace minerals and molybdenum.

In a preferred embodiment, the composition is formed by preparing a mixture comprising an effective amount of beta carotene, vitamin E, selenium, vitamin B-6, folic acid, vitamin C, magnesium, vitamin B-1, vitamin B-2, niacinamide, vitamin B-12, zinc, copper, biotin, pantothenic acid, dandelion root, acidophilus dairy free, bifidus dairy free, FOS powder, chromium polynicotinate, betaine HCl, pancreatin, papain, and pepsin.

The effective range amount of each ingredient for sixty pounds of body weight is as follows: 1,250–25,000 IU beta carotene, 25–400 IU vitamin E, 25–100 mcg selenium, 100–500 mg vitamin B-6, 400–800 mcg folic acid, 250–1,000 mg vitamin C, 125–500 mg magnesium, 12.5–50 mg vitamin B-1, 12.5–50 mg vitamin B-2, 15–60 mg niacinamide, 12.5–50 mcg vitamin B-12, 8–50 mg zinc, 250–1,000 mcg copper, 25–100 mcg biotin, 12.5–50 mg pantothenic acid, 250–2,000 mg dandelion root, 500–3,000 million cfu acidophilus dairy free, 500–3,000 million cfu bifidus dairy free, 250–500 mg FOS powder, 100–200 mcg chromium polynicotinate, 15–100 mg betaine HCl, 125–1,000 mg pancreatin, 50–250 mg papain, and (1:3000) 15–100 mg pepsin.

In a preferred embodiment, the effective amount of each ingredient for sixty pounds of body weight is as follows: 5000 IU beta carotene, 50 IU vitamin E, 25 mcg selenium, 500 mg vitamin B-6, 400 mcg folic acid, 500 mg vitamin C, 250 mg magnesium, 25 mg vitamin B-1, 25 mg vitamin B-2, 30 mg niacinamide, 25 mcg vitamin B-12, 10 mg zinc, 500 mcg copper, 50 mcg biotin, 25 mg pantothenic acid, 250 mg dandelion root, 500 million cfu acidophilus dairy free, 500 million cfu bifidus dairy free, 250 mg FOS powder, 100 mcg chromium polynicotinate, 30 mg betaine HCl, 250 mg pancreatin, 100 mg papain, and (1:3000) 30 mg pepsin.

Vitamin B-6 comprises a group of closely related compounds: pyridoxine, pyridoxal, and pyridoxamine. They are all phosphorylated in the body to pyridoxal phosphate, which functions as a coenzyme in many reactions. Vitamin B-6 helps to make and take apart many amino acids and is also needed to make serotonin, melatonin, and dopamine. Vitamin B-6 also aids in the formation of several neurotransmitters and is therefore an essential nutrient in the regulation of mental processes and possibly mood. Vitamin B-6 has been found to be helpful in almost half of all autistic children and adults included in 18 consecutive studies between 1965 and 1996. In other studies, the average amount of B6 found to be beneficial was around 8 mg of B6 per pound of body weight, per day. (This is about 500 mg/day for a 60 pound child.) B-6 is the preferred substance for this formulation, however other items such as Gotu kola, Capsicum, Alfalfa, Asparagus root, Barberry bark, Blue Cohosh, Boneset, Butcher's Broom, Chamomile, Parsley, Feverfew, Ginkgo biloba, Hops, Hydrangea root, Peppermint, Pollen, Red Clover, Red Raspberry, Rose Hips, Siberian Ginseng, Slippery Elm bark, and Spirulina also have high concentrations of B-6 could be substituted.

Folic acid is needed to make SAMe (S-adenosyl-L-methionine), which affects and may improve mood. Folate (folic acid) deficiency has been shown to lead to many conditions including psychiatric disorders. (Merck Manual 14th edition) Folic acid itself has been reported to be helpful in autism. Folic Acid is the preferred substance for this formulation, however other items such as Gotu kola, Capsicum, Alfalfa, Asparagus root, Barberry bark, Blue Cohosh, Boneset, Butcher's Broom, Chamomile, Parsley, Feverfew, Ginkgo biloba, Hops, Hydrangea root, Peppermint, Pollen, Red Clover, Red Raspberry, Rose Hips, Siberian Ginseng, Slippery Elm bark, and Spirulina also have high concentrations of Folic acid could be substituted.

Vitamin C is crucial to brain function and has been known to improve cognition and emotional symptoms. Vitamin C (ascorbic acid) is the preferred substance for this formulation, however other items such as Capsicum, Rose Hips, Alfalfa, Asparagus root, Barberry bark, Bilberry fruit, Celery seed, Chaparral, Cranberry fruit, Echinacea, Goldenseal, Parsley, Hops, Horseradish, Mullein leaf, Nettle leaf, Papaya fruit, Peppermint, Red Clover, Red Raspberry, and Yellow Dock also have high concentrations of Vitamin C could be substituted.

Magnesium has been found to enhance the effects of B-6 and protect against possible magnesium deficiency from processed foods. Magnesium has been known to reduce hyperactivity in children. Other research suggests that some children with ADD have lowered levels of magnesium. Magnesium is the preferred substance for this formulation, however other items such as Althea root, Astragalus root, Bilberry fruit, Irish moss, Boneset, Bupleururn root, Burdock root, Catnip, Chamomile, Chickweed, Devil's Claw, Elecampane root, Fennel seed, Ginger root, Gotu Kola, Hibiscus flower, Horseradish root, Horsetail, Hydrangea root, Kelp, Licorice root, Nettle, Oatgrass, Parsley, Peppermint, Red Raspberry leaf, Siberian Ginseng, Spirulina, Turneric, White Willow bark, and Yerba Santa also have high concentrations of Magnesium could be substituted.

Vitamin B-3 comes in two basic forms—niacin (also called nicotinic acid) and niacinamide (also called nicotinamide). The body uses B-3 in the process of releasing energy from carbohydrates. It is needed to form fat from carbohydrates and to process alcohol. Deficiencies of B-3 include symptoms of organic psychosis, characterized by memory impairment, disorientation, confusion, excitement, depression and mania. It also can lead to encephalopathic syndrome, characterized by clouding of consciousness, rigidity of the extremities and uncontrollable sucking and grasping reflexes. Niacinamide is the preferred substance for use in this formulation, however other items such as Gotu kola, Capsicum, Alfalfa, Asparagus root, Barberry bark, Blue Cohosh, Boneset, Butcher's Broom, Chamomile, Parsley, Feverfew, Ginkgo biloba, Hops, Hydrangea root, Peppermint, Pollen, Red Clover, Red Raspberry, Rose Hips, Siberian Ginseng, Slippery Elm bark, and Spirulina also have high concentrations of niacin could be substituted.

Copper is essential as a catalyst in many of the enzymatic pathways in the body. It is also part of the antioxidant enzyme superoxide dismutase (SOD). Copper is needed to make adenosine triphosphate (ATP), the energy on which the body runs. Copper is the preferred substance for this formulation, however other items such as Scullcap, Sage, White oak bark, Horsetail, Brewer's yeast also have high concentrations of Copper could be substituted.

Dandelion Root supports the digestive tract. It primarily works with the liver and gallbladder by stimulating digestive enzymes produced by each organ. It also stimulates digestion and can help with those who suffer from constipation and acid reflux. This herb is also high in many vitamins and minerals. Vitamins found in food are better absorbed and retained by the body. This is essential to the formulation by not only giving the digestive system support, but also by giving a natural source of vitamins and minerals. Dandelion is the preferred substance for use in this formulation, however other items such as Kelp, Sea Vegetation, Alfalfa, Trace Minerals, and Molybdenum, which also have high concentrations of minerals, could be substituted. As for digestive support, Dandelion is the preferred substance for use in this formulation, however other items such as Juniper, Aloe vera, Burdock, Ginger root, and Artichoke also have potent effects on supporting the digestive tract and could be substituted.

Probiotic (acidophilus dairy free/bifidus dairy free) bacteria favorably alter the intestinal micro-flora balance, inhibit the growth of harmful bacteria, promote good digestion, boost immune function, and increase resistance to infection. Individuals with flourishing intestinal colonies of beneficial bacteria are better equipped to fight the growth of disease-causing bacteria. Probiotics are important in finishing the digestive process and therefore can increase the absorption of nutrients.

Fructo-oligosaccharides (FOS) are naturally occurring carbohydrates that cannot be digested or absorbed by humans but support the growth of bifidobacteria, one of the beneficial bacterial strains. Friendly bacteria support digestion, elimination and the absorption of nutrients in the body.

Betaine—(hcl/gastric acid) One of the most important parts of digestion occurs in the stomach, where gastric (stomach) acid helps break down proteins for further digestion in the small intestine. This increased digestion aids in the absorption of nutrients that support the nervous system.

Papain/Pancreatin/Pepsin—Digestive enzymes—also called pancreatic enzymes—include three classes of enzymes: proteolytic enzymes needed to digest protein, lipases needed to digest fat, and amylases needed to digest carbohydrates. Pancreatic enzymes should be used with to support the digestive process. Allergies are triggered by partially undigested protein, while protoolytic enzymes reduce allergy symptoms. Proteolytic enzymes such as trypsin, chymotrypsin, and bromelain are partially absorbed by the body. Proteolytic enzymes may improve immune system ftinction, a common problem with people with allergies and nervous system weakness. Papain, Pancreatin and, Pepsin are the preferred substance for this formulation, however other items such as Papaya, and Pineapple also have high concentrations of these digestive enzymes could be substituted.

Vitamin B-1 is needed to process carbohydrates, fat, and protein. Vitamin B-1 aids in the formation of ATP. Nerve cells require vitamin B-1 in order to function normally.

Vitamin B-2 is needed to process amino acids and fats, activate Vitamin B-6 and folic acid and help convert carbohydrates into ATP. Vitamin B-2 can also act as an antioxidant.

Vitamin B-12 is needed for normal nerve cell activity, DNA replication, and production of the mood-affecting substance SAMe (S-adenosyl-L-methionine). Vitamin B-12 acts with folic acid and vitamin B-6 to control homocysteine levels. An excess of homocysteine may increase the risk of heart disease, stroke, and perhaps osteoporosis and Alzheimer's disease.

Biotin, a water-soluble B vitamin, acts as a coenzyme during the metabolism of protein, fats, and carbohydrates. Certain rare inborn diseases can leave people with depletion of biotin due to the inability to metabolize the vitamin normally.

Pantothenic acid, sometimes called vitamin B-5, is involved in the Kreb's cycle of energy production and is needed to make the neurotransmitter acetylcholine. It is also essential in producing, transporting, and releasing energy from fats. Synthesis of cholesterol (needed for vitamin D and hormone synthesis) depends on pantothenic acid. Pantothenic acid also activates the adrenal glands. Pantethine—a variation of pantothenic acid—has been reported to lower blood levels of cholesterol and triglycerides.

Chromium Polynicotinate supports the balancing of blood sugar levels. Fast peaks and valley's of blood sugar have been linked to behavioral changes in humans. Chromium is the preferred substance for this formulation, however other items such as Hibiscus flower, Spirulina, Gymnema, Oatstraw, Nettle, Red Clover, Stevia, Barley Grass, Horseradish, Juniper, Pollen, Red Clover, Brewer's Yeast, Ginkgo, Catnip, also have high concentrations of Chromium could be substituted.

Beta-carotene (Vitamin A), by maintaining healthy cell membranes, helps prevent invasion by disease-causing microorganisms. Vitamin A also stimulates immunity and is needed for formation of bone, protein, and growth hormone. Beta-carotene is a substance from plants that the body can convert to vitamin A. There is research linking vitamin A deficiency to humans with Autism and other mental health and behavioral challenges. Beta-carotene is the preferred substance for this formulation, however other items such as Spirulina, Carrot, Gotu Kola, cabbage, Barley grass, Peppermint, Yellow Dock, Parsley, Horseradish, Alfalfa, Chaparral, Capsicum, Blessed Thistle, Nettle, Yerba santa, Dandelion and Stevia also have high concentrations of Beta-carotene (Vitamin A) could be substituted.

EXAMPLE

A sample composition, for a patient weighing sixty pounds, according to the present invention is set forth below:

| INGREDIENT | AMOUNT |
| --- | --- |
| Beta Carotene | 5000 IU |
| Vitamin E | 50 IU |
| Selenium | 25 mcg |
| Vitamin B-6 | 500 mg |
| Folic Acid | 400 mcg |
| Vitamin C | 500 mg |
| Magnesium | 250 mg |
| Vitamin B-1 | 25 mg |
| Vitamin B-2 | 25 mg |
| Niacinamide | 30 mg |
| Vitamin B-12 | 25 mcg |
| Zinc | 10 mg |
| Copper | 500 mcg |
| Biotin | 50 mcg |
| Pantothenic acid | 25 mg |
| Dandelion root | 250 mg |
| Acidophilus dairy free | 500 million cfu |
| bifidus dairy free | 500 million cfu |
| FOS powder | 250 mg |
| Chromium polynicotinate | 100 mcg |
| Betaine HCL | 30 mg |
| Pancreatin | 250 mg |
| Papain | 100 mg |
| Pepsin (1:3000) | 30 mg |

It has been found that this composition is useful in treating various nervous system disorders, without adverse side effects.

Many improvements, modifications, and additions will be apparent to the skilled artisan without departing from the spirit and scope of the present invention as described herein and defined in the following claims.

What is claimed is:

1. A composition for the treatment of nervous system disorders, comprising therapeutically effective amounts of vitamin B-6, folic acid, vitamin C, magnesium, vitamin B-3, copper, probiotics, fructo-oligosaccharide, betaine, pancreatin, papain, pepsin, vitamin B-1, vitamin B-2, vitamin B-12, biotin, pantothenic acid, chromium polynicotinate and a digestive support ingredient selected from the group consisting of dandelion root, juniper, aloe vera, burdock, ginger root, artichoke, and kelp.

2. A composition for the treatment of nervous system disorders as in claim 1, wherein said digestive support ingredient is dandelion root.

3. A composition for the treatment of nervous system disorders as in claim 1, wherein said probiotics are acidophilus dairy-free and bifidus dairy-free.

4. A composition for the treatment of nervous system disorders as in claim 1, wherein vitamin B-3 is in the form of niacinamide.

5. A composition for the treatment of nervous system disorders as in claim 1, wherein said vitamin B-6 is derived from one or more of the items selected from the group consisting of Gotu kola, Capsicum, Alfalfa, Asparagus root, Barberry bark, Blue Cohosh, Boneset, Butcher's Broom, Chamomile, Parsley, Feverfew, Ginkgo biloba, Hops, Hydrangea root, Peppermint, Pollen, Red Clover, Red Raspberry, Rose Hips, Siberian Ginseng, Slippery Elm bark, and Spirulina.

6. A composition for the treatment of nervous system disorders as in claim 1, wherein said folic acid is derived from one or more of the items selected from the group consisting of Gotu kola, Capsicum, Alfalfa, Asparagus root, Barberry bark, Blue Cohosh, Boneset, Butcher's Broom, Chamomile, Parsley, Feverfew, Ginkgo biloba, Hops, Hydrangea root, Peppermint, Pollen, Red Clover, Red Raspberry, Rose Hips, Siberian Ginseng, Slippery Elm bark, and Spirulina.

7. A composition for the treatment of nervous system disorders as in claim 1, wherein said vitamin C is derived from one or more of the items selected from the group consisting of Capsicum, Rose Hips, Alfalfa, Asparagus root, Barberry bark, Bilberry fruit, Celery seed, Chaparral, Cranberry fruit, Echinacea, Goldenseal, Parsley, Hops, Horseradish, Mullein leaf, Nettle leaf, Papaya fruit, Peppermint, Red Clover, Red Raspberry, and Yellow Dock.

8. A composition for the treatment of nervous system disorders as in claim 1, wherein said magnesium is derived from one or more of the items selected from the group consisting of Althea root, Astragalus root, Bilberry fruit, Irish moss, Boneset, Bupleururn root, Burdock root, Catnip, Chamomile, Chickweed, Devil's Claw, Elecampane root, Fennel seed, Ginger root, Gotu Kola, Hibiscus flower, Horseradish root, Horsetail, Hydrangea root, Kelp, Licorice root, Nettle, Oatgrass, Parsley, Peppermint, Red Raspberry leaf, Siberian Ginseng, Spirulina, Turneric, White Willow bark, and Yerba Santa.

9. A composition for the treatment of nervous system disorders as in claim 1, wherein said vitamin B-3 is derived from one or more of the items selected from the group consisting of Gotu kola, Capsicum, Alfalfa, Asparagus root, Barberry bark, Blue Cohosh, Boneset, Butcher's Broom, Chamomile, Parsley, Feverfew, Ginkgo biloba, Hops, Hydrangea root, Peppermint, Pollen, Red Clover, Red Raspberry, Rose Hips, Siberian Ginseng, Slippery Elm bark, and Spirulina.

10. A composition for the treatment of nervous system disorders as in claim 1, wherein said copper is derived from one or more of the items selected from the group consisting of Scullcap, Sage, White oak bark, Horsetail, and Brewer's yeast.

11. A composition for the treatment of nervous system disorders as in claim 1, wherein said chromium polynicotinate is derived from one or more of the items selected from the group consisting of: Hibiscus flower, Spirulina, Gymnema, Oatstraw, Nettle, Stevia, Barkley Grass, Horseradish, Juniper, Pollen, Red Clover, Brewer's Yeast, Ginkgo and Catnip.

12. A composition for the treatment of nervous system disorders as in claim 1, wherein said composition also comprises: beta carotene, vitamin E, selenium, zinc, sea vegetation, alfalfa, trace minerals and molybdenum.

13. A composition for the treatment of nervous system disorders as in claim 1, wherein said composition is in the form of capsule, tablet or powder.

* * * * *